United States Patent [19]

Avenia et al.

[11] 4,108,973

[45] Aug. 22, 1978

[54] IMMUNOASSAY FOR CATECHOLAMINES

[75] Inventors: Richard William Avenia, Nutley; Benjamin Pecherer, Montclair, both of N.J.

[73] Assignee: Hoffmann-La Roche Inc., Nutley, N.J.

[21] Appl. No.: 717,786

[22] Filed: Aug. 25, 1976

[51] Int. Cl.$^2$ .................. G01N 33/16; A61K 43/00
[52] U.S. Cl. ..................... 424/1; 23/230 B; 260/112 R
[58] Field of Search ............... 424/111.5; 260/112 R; 23/230 B

[56] References Cited

U.S. PATENT DOCUMENTS

| | | | |
|---|---|---|---|
| 3,704,282 | 11/1972 | Spector | 424/12 |
| 3,878,187 | 4/1975 | Schneider et al. | 424/12 |
| 3,996,344 | 12/1976 | Gross | 424/12 |
| 4,016,146 | 4/1977 | Soares | 424/12 |

*Primary Examiner*—Benjamin R. Padgett
*Assistant Examiner*—Christine M. Nucker
*Attorney, Agent, or Firm*—Samuel L. Welt; George M. Gould; George M. Gould

[57] ABSTRACT

Epinephrine and norepinephrine type catecholamines can be individually assayed by immunoassay directed against the side chain common to these compounds by employing an oxidation procedure which selectively converts one or more of the epinephrine or norepinephrine type catecholamines to another compound which is not bound by the antibody. By measuring the difference between the total epinephrine or norepinephrine type catecholamine content and that after each of the oxidation steps, it is possible to determine the quantity of individual catecholamines of either type present in the original sample.

12 Claims, No Drawings

IMMUNOASSAY FOR CATECHOLAMINES

BACKGROUND OF THE INVENTION

The use of radioimmunoassay for the detection of catecholamines has been described in U.S. Pat. No. 3,704,282 issued Nov. 28, 1972. While this is an extremely sensitive assay procedure, the antibody utilized therein cannot readily distinguish between closely related catecholamines and thus one obtains only an indication of total catecholamine content in the sample. Thus it would not be possible using such procedure to determine the specific presence of the individual concentrations of epinephrine type catecholamines such as epinephrine, metanephrine, synephrine or phenylephrine or norepinephrine type catecholamines such as norepinephrine, normetanephrine, octopamine or norphenephrine in a sample.

The preparation of antigens useful for eliciting antibodies selective to amphetamine analogs is disclosed in U.S. Pat. No. 3,878,187 issued Apr. 15, 1975. The antigen comprises an amphetamine hapten linked to an immunogenic protein through an alkylene oxycarbonyl linking group.

An improved fluorometric assay of catecholamines has been described by Laverty and Taylor, Analytical Biochemistry 22, 269 (1968). In such technique the catecholamines in a sample are oxidized with iodine to produce a fluorescent indole derivative which is then detected in a fluorometer. To a limited extent it is possible to measure an individual catecholamine in the presence of other related compounds. This requires the use of different oxidation pH's, different treatments of the final solution and different wavelength maxima. However, cross-interference can still arise even with the use of such conditions and thus only a very few catecholamines can actually be detected in admixture without the use of chemical separation prior to detection.

DESCRIPTION OF THE INVENTION

The present invention relates to an improved assay method which allows for the individual quantitative detection of epinephrine type catecholamines, i.e., epinephrine, metanephrine, synephrine and phenylephrine, or norepinephrine type catecholamines, i.e., norepinephrine, normetanephrine, octopamine and norphenephrine, when present in admixture in a sample. In particular, the method of the present invention utilizes an oxidation procedure whereby under different conditions of pH and temperature one or more selected epinephrine-type or norepinephrine-type catecholamines present in order of increasing lability to oxidation is converted to a form not immunoreactive with an antibody specific to that catecholamine type. The initial sample and each of the reaction products from the oxidation procedure are assayed after treatment with the sulfite reducing agent by immunoassay with an antibody specific for the epinephrine or norepinephrine side chain. Since the antibody used in the assay does not have an affinity for the products produced in the selective oxidation step, the concentration of the specific epinephrine or norepinephrine type catecholamine being converted can be determined by subtracting the catecholamine content found in a sample oxidized under one condition from the catecholamine content determined in a duplicate sample without oxidation or in a duplicate sample oxidized under a less rigorous condition.

The antibody employed in the aforesaid immunoassay can be obtained in a manner known per se. Thus, for example, haptenic compounds of the formula

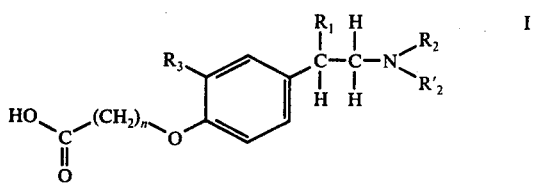

wherein $R_1$ is hydrogen or hydroxy; $R_2$ is hydrogen or lower alkyl; $R_2'$ is hydrogen or a conventional amine protecting group; and $R_3$ is hydrogen, hydroxy or lower alkoxy; and $n$ is an integer from 1 to 3 are utilized in the preparation of an antigen.

Preferred haptenic compounds for use in the practice of the present invention are derived from synephrine for the epinephrine type catecholamines and octopamine for the norepinephrine type catecholamines.

The t-butoxycarbonyl group is employed as a protective group in compounds of formula I to serve to prevent self-condensation reactions during further transformations in the preparation of the needed antigens. The t-butoxycarbonyl group can be readily cleaved to yield an antigen wherein $R_2'$ is hydrogen.

In order to prepare the antigens needed in the present invention, it is necessary that the hapten of formula I be covalently bonded through the carboxylic group to a conventional immunogenic carrier material. As used herein, the term "immunogenic carrier material," is meant to include those materials which have the property of independently eliciting an immunogenic response in a host animal and which can be covalently coupled to the above described haptens. Suitable carrier materials include for example, proteins; natural or synthetic polymeric compounds such as polypeptides, e.g., polylysine or copolymers of amino acids, polysaccharides; and the like. Particularly preferred carrier materials are proteins and polypeptides, especially proteins.

The identity of the protein material utilized in the preparation of an antigen useful in the instant invention is not critical. Examples of suitable proteins useful in the practice of this invention include mammalian serum proteins such as, for example, human gamma globulin, human serum albumin, bovine serum albumin, methylated bovine serum albumin, rabbit serum albumin and bovine gamma globulin. Other suitable protein products will be suggested to one skilled in the art. It is generally preferred but not necessary that proteins be utilized which are foreign to the animal hosts in which the resulting antigen will be employed.

The covalent coupling of the hapten to the immunogenic carrier material can be carried out in a manner well known in the art for establishing amide bonds. However, to ensure an adequate degree of coupling under the mildest possible conditions so as to minimize any possible deleterious effect on the carrier material it may be desirable to convert the hapten of formula I to an isolatable activated form prior to coupling. One particularly preferred isolatable activated form is the N-hydroxysuccinimide ester as indicated by formula II:

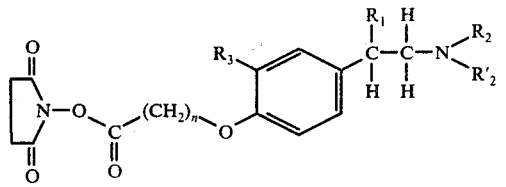

wherein $R_1$, $R_2$, $R_2'$, $R_3$ and $n$ are as above.

Other suitable isolatable activated derivatives include the p-nitrophenyl esters; acylimidazoles; and so forth. Other methods for coupling may be employed wherein the activated intermediates need not be isolated. Such methods include the mixed anhydride method, use of EEDQ (N-ethoxycarbonyl-2-ethoxy-1,2-dihydroquinoline) as coupling agent and the like.

The coupling of the hapten either as the free acid of formula I or more preferably as an activated derivative, e.g., formula II, to the immunogenic carrier material can be readily accomplished utilizing techniques now well known in the art for establishing amide bonds. Thus, for example, one such technique would involve dissolving the carrier material and coupling agent in a suitable inert solvent followed by adding the desired hapten of formula I. The reaction may be conducted in a temperature in the range of from about 0° C. to about 50° C. although higher or lower temperatures might be employed depending on the nature of the reactants. A most preferable temperature is about room temperature.

The coupling agent which may be used in the aforesaid reaction will be selected from those commonly employed in organic chemistry for initiating amide bond formation. A particularly suitable group of coupling agents comprises the carbodiimides, most preferably dicyclohexylcarbodiimide or 1-ethyl-3-(3-dimethylaminopropyl)carbodiimide. The molar ratio of the hapten to the carrier material will, of course, depend on the identity of the hapten utilized and the protein selected for the reaction.

Conventional conditions for the coupling reaction can be employed. Thus when utilizing carbodiimides as coupling agents, it is desirable to utilize a slightly acidic reaction medium for this step, e.g., a medium having a pH in the range of from about 3 to 6.5, most preferably in the range of from about 4 to 6.5. Upon completion of the reaction, the excess hapten molecules may be removed by dialysis.

As indicated previously, one preferred technique for preparing the antigens of the present invention is to first prepare and isolate an activated derivative, i.e., a compound of formula II, and then to react this compound with the carrier material to form the blocked antigen. Such activated derivatives are conveniently prepared by reacting a compound of formula I with a desired activating compound, such as N-hydroxysuccinimide, and a coupling agent, such as dicyclohexylcarbodiimide, in an inert solvent. The reaction is usually allowed to proceed for 16–60 hours at reduced temperatures (0°–5° C.). The activated derivative may then be isolated by filtering off the by-product, dicyclohexylurea, and distilling off the solvent.

The hapten may then be coupled to the carrier material by contacting the activated derivative with the chosen carrier material. When the activated derivative is the N-hydroxysuccinimide ester and the carrier material is bovine serum albumin, this may be accomplished by adding the activated derivative in a water-miscible solvent to an aqueous solution of the carrier material containing a base, such as sodium bicarbonate.

Another method of coupling carrier protein to hapten (formula I) is by activating the carboxyl group of the hapten without isolation of an intermediate and adding the activated hapten to the carrier protein. An example of such a reaction is the mixed anhydride obtained by reaction with isobutylchloroformate. The hapten is dissolved in an anhydrous, water-miscible organic solvent, usually dioxane, and the solution is neutralized with an equimolar quantity of triethylamine. After stirring at room temperature, the temperature of the mixture is reduced to between 0° and 8° C. An equimolar quantity plus 10% excess of isobutylchloroformate is then added and stirring is continued. Meanwhile, the carrier protein, e.g., bovine serum albumin, is dissolved in water and the pH is adjusted to 9.0 with NaOH. The quantity of carrier used is equivalent to the molar quantity of hapten divided by the theoretical number of reactive groups on the carrier. Organic solvent is added to the carrier solution and the solution is cooled to between 0° and 8° C. The solution is then added to the activated hapten and coupling is allowed to proceed for 30 minutes to overnight. The final ratio of organic solvent to water is 1:1.

The mixture is then adjusted to neutrality, the aqueous-organic solvent is removed and aqueous solution is effected. After dialysis and lyophilization, the amine-protecting group is removed.

Following coupling of a compound of either formula I or formula II to the carrier material, it is necessary to remove the protective group (R' in formulae I and II), in order to restore the free primary or secondary amino function. In the case of the t-butoxycarbonyl protective group, this may be conveniently achieved by treating the material with trifluoroacetic acid in dichloromethane at room temperature. The relative amounts of trifluoroacetic acid and dichloromethane and the time duration of the treatment may be varied to suit particular cases. In general, from one to three volumes of dichloromethane per volume of trifluoroacetic acid and reaction times of 30 to 60 minutes have been found to give good results.

The aforesaid antigens may be utilized to induce formation of antibodies specific to epinephrine or norepinephrine type catecholamines in host animals by injecting the antigen in such a host, preferably using an adjuvant. Improved titers can be obtained by repeated injections over a period of time. Suitable host animals for this purpose include mammals such as rabbits, horses, goats, guinea pigs, rats, cows, sheep, etc. The resulting antisera will contain antibodies which will selectively complex with the epinephrine or norepinephrine type catecholamines depending on the hapten utilized to prepare the antigen employed in the host innoculation.

The immunoassay utilized to detect the epinephrine or norepinephrine type catecholamines in each step of the present method may be selected from immunoassays well known in the art. A particularly preferred immunoassay for this purpose is a radioimmunoassay such as described in U.S. Pat. Nos. 3,704,282 or 3,709,868 utilizing the epinephrine or norepinephrine type catecholamine specific antibody discussed above. Alternatively, it is also possible to utilize other immunoassays such as, for example, an enzyme amplification assay described in U.S. Pat. No. 3,817,837 or a free radical assay using spin labeled compounds as described in U.S. Pat. No. 3,690,834.

The specificity of an epinephrine type catecholamine antibody suitable for use in the practice of the present method is set forth below in Table 1:

aqueous sulfite solution as before, adjust pH to desired range for immunoassay and then conduct an immunoassay on the reaction mixture to determine remaining epinephrine type catecholamine concentration (phenylephrine).

ANTIBODY SPECIFICITY $$R_3\text{-phenyl}(R_2, R_1)\text{-C}(R_4,H)\text{-C}(H,R_5)\text{-N}(R_6,H)$$

| COMPOUND | $R_1$ | $R_2$ | $R_3$ | $R_4$ | $R_5$ | $R_6$ | 50% INHIBITION OF Ab-7$^{123}$ dl-Met COMPLEX ng. |
|---|---|---|---|---|---|---|---|
| l-Epinephrine | H | OH | OH | OH | H | $CH_3$ | 0.250 |
| dl-Metanephrine | H | OH | $OCH_3$ | OH | H | $CH_3$ | 0.050 |
| dl-Synephrine | H | OH | H | OH | H | $CH_3$ | 0.100 |
| Epinine | H | OH | OH | H | H | $CH_3$ | 0.350 |
| l-Phenylephrine (Neosynephrine) | OH | H | H | OH | H | $CH_3$ | 0.060 |
| l-Norepinephrine | H | OH | OH | OH | H | H | > 500 |
| Dopamine | H | OH | OH | H | H | H | > 500 |
| Amphetamine | H | H | H | H | $CH_3$ | H | > 500 |
| Methamphetamine | H | H | H | H | $CH_3$ | $CH_3$ | > 500 |
| Ephedrine | H | H | H | OH | $CH_3$ | $CH_3$ | > 500 |
| Isoproterenol | H | OH | OH | OH | H | $C(CH_3)_2H$ | > 500 |
| DOPA | H | OH | OH | H | COOH | H | > 500 |
| VYA | | | | | CH | | > 500 |

VYA structure: $R_2$, $R_3$-phenyl-C(CH)-C=CH-H

Sezotosin: OH-indane-$CH_2$-$CH_2$-N ... > 500

A suitable procedure for conducting the method of the present invention can be summarized as follows:

(A) test a sample aliquot with immunoassay to determine total epinephrine type catecholamine content (epinephrine + metanephrine + synephrine + phenylephrine);

(B) adjust another sample aliquot to pH 7.4 with phosphate buffer and treat with 0.1N iodine (in aqueous solution, complexed with sodium iodide) for 5 mintues at 4° C. so as to selectively convert epinephrine to the adrenochrome form; treat the reaction mixture with excess aqueous sodium sulfite (as a 10% solution) to reduce the unreacted iodine; if necessary, adjust pH to a range required for immunoassay with buffer and run the immunoassay on the reaction mixture to determine remaining epinephrine type catecholamine content (metanephrine + synephrine + phenylephrine);

(C) adjust another sample aliquot to pH 8.6 with phosphate buffer and treat with iodine as above for 5 minutes at 4° C. to selectively convert both epinephrine and metanephrine to the adrenochrone form, treat the reaction mixture with excess aqueous sulfite solution as before, adjust pH to desired range for immunoassay (pH 7.4 with the antibody described above) and then conduct immunoassay on the reaction mixture to determine remaining epinephrine type catecholamine concentration (synephrine + phenylephrine);

(D) adjust an additional sample aliquot to pH 9.2 with carbonate-bicarbonate buffer and treat with iodine as above for 5 minutes at room temperature to selectively convert epinephrine, metanephrine and synephrine to the cyclized form, treat the reaction mixture with excess The phenylephrine content of the sample is thus determined directly by the immunoassay results in Step D. Epinephrine content is derived by subtracting the epinephrine type catecholamine content found in Step B from the total epinephrine type catecholamine content found by direct immunoassay of the sample in Step A. Similarly, metanephrine content is determined by subtracting the concentration level found in Step C from that of Step B. Finally, synephrine content is obtained by subtracting the result of Step D from that of Step C.

The immunoassay described above is also useful for assaying for individual norepinephrine type catecholamines when an antibody having specificity to the norepinephrine type side-chain is used. Thus, in Step (A) above a sample aliquot is tested to determine total norepinephrine type catecholamine content (norepinephrine + normetanephrine + octopamine + norphenephrine). Step (B) is run under the same conditions and in the same manner and provides the remaining norepinephrine type catecholamine content (normetanephrine + octopamine + norphenephrine). Similarly Step (C) is run in the same manner as above to provide the octopamine + norphenephrine concentration. Finally, Step (D) is conducted in an identical manner to give norphenephrine concentration. Finally, the individual norepinephrine type catecholamine concentrations are calculated as above for the respective cases in the epinephrine type catecholamine series, i.e., norphenephrine is determined from Step (D), norepinephrine is determined by subtracting the content of Step (B) from that of Step (A), normetanephrine content is determined by subtracting the level of Step (C) from that of step (B), and finally octopamine content is obtained by subtracting the result of Step (D) from that of Step (C).

The individual epinephrine or norepinephrine type catecholamine contents of various test samples can be determined by the method of the present invention. Examples of such test samples include biological fluids such as urine, blood, tissue extracts and the like. In some instances pretreatment of the test sample may be required to meet the specific needs of the immunoassay employed. Thus, for example, deproteinization in a manner known per se may be required before assay is initiated.

As used herein the term "lower alkyl" is meant to include straight or branched chain hydrocarbon groups having 1 to 7, preferably 1 to 4 carbon atoms such as methyl, ethyl, n-propyl, n-butyl, etc. The term "lower alkoxy" is meant to include lower alkyloxy moieties where lower alkyl is as above. A most preferred lower alkyl group is methyl and a most preferred lower alkoxy group is methoxy.

EXAMPLE 1 t-Butyl ester of rac.
N-(4,alpha-dihydroxyphenethyl)-N-methyl carbamic acid 41.8 g. (0.28 moles) of rac. synephrine and 53.6 g. (0.375 moles) of t-butoxycarbonyl azide were stirred together in 1 l. of 50% aqueous dioxane in the presence of 4 g. of magnesium oxide for 22 hours at 40°–45° C. The dioxane was distilled from the pale amber solution and to the residue, 500 ml. of water was added. On chilling, 58.7 g. of solid separated, m.p. 141.5°–143.5° (after drying at 100° for 3 hours). Recrystallization of a sample of this material gave white crystals of m.p. 141°–141.5° C. of the above captioned product.

Microanalysis: C, 62.88; H, 7.83; N, 5.19
Calc. for $C_{14}H_{20}NO_4$: C, 62.90; H, 7.92; N, 5.24

EXAMPLE 2

Ethyl ester of rac.
4-[2-(N-t-butoxycarbonyl-N-methylamino)-1-hydroxyethyl]phenoxyacetic acid 26.7 g. of the t-butyl ester of rac. (4,alpha-dihydroxyphenethyl)-N-methyl carbamic acid (0.1 mole) was dissolved in 250 ml. of hexamethylphosphoric triamide and to the stirred solution under nitrogen was added 2.4 g. of sodium hydride (0.1 mole) in small portions. The mixture was stirred until hydrogen evolution ceased (approx. 3 hours). To this stirred solution was added in a single portion 17.0 g. of ethyl bromoacetate (0.1 mole) in 25 ml. of benzene. The external temperature rose from 7° to 19° C. The mixture was approximately neutral in 10 minutes. Water and ice (500 ml.) were added to the mixture, the slightly turbid mixture was extracted five times with 150 ml. portions of ether, the combined ether extracts washed with a few small portions of water and dried over magnesium sulfate. After removal of the drying agent, the solvent was distilled in the rotary evaporator. The residue, 39 g. of viscous syrup, resisted efforts to crystallize and was used as in the hydrolysis to the free acid described below.

EXAMPLE 3

Rac.
4-[2-(N-t-butoxycarbonyl-N-methylamino)-1-hydroxyethyl]phenoxyacetic acid

The corresponding ethyl ester of Example 2 was hydrolyzed by suspending the material in water at 80°–85° C. and adding 10% sodium hydroxide solution until a permanent pH of 9-10 was obtained. After acidification with 20% citric acid solution to pH 3, the mixture was extracted with several portions of chloroform. The combined chloroform extracts were dried, the drying agent removed by filtration and the solvent distilled in the rotary evaporator. A syrup was obtained which would not crystallize. It was therefore converted to the crystalline S-benzylthiuronium salt in the following manner: A weighed sample of the syrupy acid was treated with sufficient sodium hydroxide to form the sodium salt (pH 7.5–8.0). To this solution was added a concentrated solution of S-benzylthiuronium chloride, whereupon a precipitate formed. The solid was recovered, washed with cold water and then recrystallized from water to obtain white crystals of m.p. 163°–165° C. Analysis indicated that the crystals were the S-benzylthiuronium salt of the above named acid.

Microanalysis: Found - C, 58.64; H, 6.77; N, 8.55
Calcd. for $C_{16}H_{22}NO_6 \cdot C_8H_{11}SN_2$: C, 58.60; H, 6.77; N, 8.60

EXAMPLE 4

N-Hydroxysuccinimide ester of rac.
4-[2-(N-t-butoxycarbonyl-N-methylamino)-1-hydroxyethyl]phenoxyacetic acid 3.25 g. (0.01 moles) of the syrupy acid described above in Example 3 was dissolved in 40 ml. of dimethoxyethane together with 1.15 g. of N-hydroxysuccinimide (0.01 moles) and to this solution was added 2.06 g. of dicyclohexylcarbodiimide (0.01 mole) whereupon the solution warmed perceptibly. The mixture was then stored at 5° C. for 21 hours. The dicyclohexylurea that had separated was removed by filtration, the filter cake washed with a little dimethoxyethane, and the combined filtrates distilled in the rotary evaporator. There remained 3.70 g. of a turbid syrup that was dissolved in 75 ml. of toluene and the undissolved dicyclohexylurea that had separated was removed by filtration. Distillation of the solvent left a syrup that was dissolved in 50 ml. of 2-propanol; 60°–90° petroleum ether was added to turbidity and the solution stored at 5° C. for 5 days. The crystals that separated were recovered, yield 2.5 g. of m.p. 106°–108.5° C.

Microanalysis: C, 56.58; H, 6.38; N, 6.73
Calc. for $C_{20}H_{26}N_2O_2$: C, 56.87; H, 6.20; N, 6.63

EXAMPLE 5 t-Butyl ester of rac.
N-(4,alpha-dihydroxyphenethyl)carbamic acid 47.5 g. of rac. octopamine hydrochloride (0.25 moles) and 53.6 g. of t-butoxycarbonylazide (0.375 moles) were stirred together in a mixture of one liter of 50% aqueous dioxane and 12 g. of magnesium oxide (0.30 moles) at 37°–45° C. for 21 hours under nitrogen. The dioxane was distilled from the solution in the rotary evaporator. After adjusting the pH to 6 with acetic acid, the solution was extracted five times with 200 ml. portions of chloroform. The combined chloroform extracts were washed with a little water, the solution dried, then the solvent distilled leaving 59.0 g. of crystalline solid of m.p. 146°-148° C. After recrystallization from a mixture of ethyl acetate and 60°-90° petroleum ether, the product melted at 147°-148° C.

Microanalysis: C, 61.71; H, 7.70; N, 5.47
Calc. for $C_{13}H_{19}NO_4$: C, 61.65; H, 7.56; N, 5.33

EXAMPLE 6

Ethyl ester of rac. 4-[2-(N-t-butoxycarbonylamido)-1-hydroxyethyl]-phenoxyacetic acid 23.5 g. of the t-butyl ester of rac. N-(4, alpha-dihydroxyphenethyl)carbamic acid (0.1 moles) was dissolved in 350 ml. of hexamethylphosphoric triamide and to the stirred solution under nitrogen was added 2.4 g. of sodium hydride (0.1 moles) in small portions. The mixture was stirred until hydrogen evolution ceased. To this stirred solution was then added in a single portion 17.0 g. of ethyl bromoacetate (0.1 moles) in 25 ml. of benzene. The external temperature rose from 7° to 19° C. The mixture was approximately neutral in ten minutes. Water and ice (500 ml.) were added to the mixture, the slightly turbid mixture was extracted five times with 150 ml. portions of ether, the combined ether extracts washed with a few small portions of water and dried over magnesium sulfate. After removal of the drying agent, the solvent was distilled in the rotary evaporator. The residue, 31.7 g. of an amber syrup, was dissolved in hot carbon tetrachloride and on cooling crystals were deposited. These crystals melted at 56°-59° C.; after drying in high vacuum at 45° C. the crystals were transformed to a colorless glass.

Microanalysis: Found: C, 60.10; H, 7.32; N, 4.22
Calc. for $C_{17}H_{25}NO_6$: C, 60.10; H, 7.42; N, 4.13

EXAMPLE 7

Rac. 4-(2-t-butoxycarbonamido-1-hydroxyethyl)phenoxyacetic acid

The product of Example 6 was hydrolyzed by suspending it in water at 80°-85° C. and adding 10% sodium hydroxide solution until a permanent pH of 9-10 was obtained. After acidification with 20% citric acid solution to pH 3, the solution was extracted twice with 100 ml. portions of chloroform. The combined chloroform extracts were dried, the drying agent removed by filtration and the solvent distilled in the rotary evaporator. A pale amber syrup resulted. The syrup was dissolved in hot 60°-90° petroleum ether and on cooling crystals separated. These off-color crystals, 22.55 g., were dissolved in 100 ml. of acetonitrile, treated with charcoal, filtered and from the cooled filtrate 8.9 g. of solid was obtained, m.p. 98°-101° C. After one more recrystallization from acetonitrile using decolorizing carbon, 6.65 g. of slightly grayish crystals were obtained, m.p. 109°-111° C.

Microanalysis: Found: C, 57.90; H, 6.88; N, 4.85
Calc. for $C_{15}H_{21}NO_6$: C, 57.87; H, 6.80; N, 4.50

EXAMPLE 8

The N-hydroxysuccinimide ester of rac. 4-[2-(N-t-butoxycarbonyl-N-methylamino)-1-hydroxyethyl]-phenoxy acetic acid was coupled to bovine serum albumin (BSA) following the procedure set forth below.

A total of 300 mg. (0.00447 mmoles) of bovine serum albumin (BSA) in 12 ml. of water was treated with 6 ml. of a 0.5 M solution of sodium bicarbonate and then with 6 ml. of dimethoxyethane containing 60 mg. (0.075 mmoles) of the N-hydroxysuccinimide ester of rac. 4-[2-(N-t-butoxycarbonyl-N-methylamino)-1-hydroxyethyl]phenoxy acetic acid. The mixture was stirred for three hours at room temperature, 96 ml. of ethanol was added and the solution evaporated to a small volume. The residue was then dialyzed against 200 volumes of water for three days with two changes per day and then the protected antigen was lyophilized. A second run was carried out under the same conditions as above with the exception that 162 mg. of the activated ester was employed.

Removal of the t-butoxycarbonyl protecting group was accomplished by stirring 50 mg. of the protected antigen with 50% trifluoroacetic acid in 50 ml. of methylene chloride for 1 hour at room temperature. The trifluoroacetic acid was then removed by flash evaporation. The residue was washed with water followed by evaporation. The residue was then taken up in water and lyophilized to yield the desired antigen.

Examination of the antigen produced from both runs using protein analysis and differential U.V. spectral analysis indicated that the antigen of run 1 contained 14 moles of hapten per mole of BSA (17% substitution based on 85 theoretically available amino groups) while the antigen of run 2 contained 25 moles of hapten per mole of BSA (29% substitution). This antigen is used to elicit antibody specific for epinephrine, metanephrine, synephrine and phenylephrine.

EXAMPLE 9

Rac. 4-(2-t-butoxycarbonamido-1-hydroxyethyl)-phenoxyacetic acid was coupled to BSA utilizing the mixed anhydride method as follows.

A total of 39.46 mg. (0.1269 mmoles) of the protected hapten was added to 1 ml. of dry dioxane followed by the addition of 0.1269 mmoles of triethylamine in 0.5 ml. dioxane. The mixture was stirred at room temperature for 10 minutes and then cooled to 8° C. 0.1395 mmoles of isobutylchloroformate in 0.5 ml. dioxane was added and the solution was stirred for 20 minutes.

In a separate flask 100 mg. of BSA was dissolved in 10 ml. of water, the pH was adjusted to 9 with sodium hydroxide and 8 ml. of dioxane was added slowly with stirring. The solution was cooled to 8° C. and the protected hapten solution from above was added and stirred 30 minutes at 8° C. and then overnight at 4° C. at pH 9.

The solution was then treated with acid to neutrality, the solvent removed and the residue taken up in 5 ml. water (NaOH added to effect solution). Five milliliters of this solution was dialyzed successively against 6000 ml. each of 0.5N NaOH, 0.1N NaOH and $H_2O$ (2 times). The amine-blocked antigen solution was removed and lyophilized. The t-butoxycarbonyl group was removed with trifluoroacetic acid as described in Example 8.

Analysis of the resulting antigen by protein determination and U.V. analysis indicated that there were 64 moles of hapten per mole of BSA. The antigen so produced is useful in eliciting antibodies which recognize norepinephrine, normetanephrine, octopamine and norphenephrine when injected into suitable animals.

EXAMPLE 10

Immunization and Bleeding

For immunization of rabbits, 10 mg. of each of the products of Example 8 or Example 9 was dissolved in 1 ml. of phosphate buffered saline and emulsified with 1 ml. of complete Freund's adjuvant. The second inoculation was given three weeks later and consisted of 1.5 mg. immunogen in 1 ml. PBS emulsified with 1 ml. of complete Freund's adjuvant. The third injection, five weeks after the first, employed the same concentration of antigen but was in incomplete Freund's adjuvant. Immunizations were by the subcutaneous route.

Test bleedings were taken after five weeks and at monthly intervals thereafter. Thirty ml. of blood was drawn and the serum separated by standard techniques.

Assay Procedure

A competitive binding radioimmunoassay procedure is used similar to that described in U.S. Pat. No. 3,704,282. An incubation volume of either 0.5 or 1.0 ml. is used and antibody-label complex is separated from free label by precipitation with saturated

Preparation of Labeled Compounds

Radiolabeled epinephrine type catecholamines useful in a radioimmunoassay for epinephrine type catecholamines are either commercially available (epinephrine $^3H$) or else can be prepared by using methods well known in the art such as the chloramine T method for introducing iodine labels (synephrine $^{125}I$; metanephrine $^{125}I$ and phenylephrine $^{125}I$).

Similarly norepinephrine type catecholamines radiolabeled with tritium are commercially available (norepinephrine $^3H$ and normetanephrine $^3H$) or can be prepared by the chloramine T method (normetanephrine $^{125}I$, octopamine $^{125}I$ or norphenephrine $^{125}I$).

We claim:

1. A method for assaying for individual epinephrine type catecholamines selected from epinephrine, metanephrine, synephrine and phenylephrine in a test sample which method comprises in combination:
   (A) determining the total epinephrine type catecholamine concentration by conducting an immunoassay on said test sample utilizing an antibody having specificity for epinephrine type catecholamines;
   (B) treating an aliquot of said test sample with iodine at pH 7.4 so as to selectively convert any epinephrine present in said test sample to a form which is not bound by said antibody, treating said aliquot with excess aqueous sulfite solution so as to reduce any remaining iodine, adjusting the pH of the resulting solution to that required for said immunoassay and then determining the epinephrine type catecholamine concentration by conducting said immunoassay on said resulting solution representing the sum total of metanephrine, synephrine and phenylephrine present in said test sample;
   (C) treating a second aliquot of said test sample with iodine at pH 8.6 so as to selectively convert any epinephrine and metanephrine present in said test sample to forms which are not bound by said antibody, treating said aliquot with excess aqueous sulfite solution, adjusting the pH to a level compatible for said immunoassay and then determining the concentration of epinephrine type catecholamines by conducting said immunoassay on said test solution, said concentration representing the sum total of synephrine and phenylephrine present in said test sample; and
   (D) treating a third aliquot of said test sample with iodine at pH 9.2 so as to selectively convert any epinephrine, metanephrine and synephrine present in said test sample to forms which are not bound by said antibody, treating said aliquot with excess aqueous sulfite solution, adjusting the pH to a level compatible for said immunoassay and then determining the concentration of epinephrine type catecholamine by conducting said immunoassay on said test sample, said concentration representing the phenylephrine present in said test sample;
   wherein the concentration of epinephrine is determined by subtracting the concentration found in Step (B) above from that of Step (A); the concentration of metanephrine is determined by subtracting the concentration found in Step (C) above from that of Step (B); and the concentration of synephrine is determined by subtracting the concentration found in Step (D) above from that of Step (C).

2. The method of claim 1 wherein the pH of the iodination treating of Steps (B) and (C) are maintained with phosphate buffer while the pH of the iodination treatment of Step (D) is maintained with carbonate-bicarbonate buffer.

3. The method of claim 1 wherein said immunoassay utilized is radioimmunoassay.

4. The method of claim 1 wherein the sample is first deproteinized.

5. An antigen consisting essentially of rac. 4-[2-N-methylamino-1-hydroxyethyl]phenoxy acetic acid covalently bonded to an immunogenic carrier material.

6. The antigen of claim 5 wherein said immunogenic carrier material is bovine serum albumin.

7. An antibody specific for epinephrine type catecholamines, said antibody being elicited by an antigen comprising rac. 4-[2-N-methylamino)-1-hydroxyethyl]-phenoxy acetic acid covalently bonded to an immunogenic carrier material.

8. An antigen consisting essentially of rac. 4-(2-amino-1-hydroxyethyl) phenoxy acetic acid covalently bonded through the carboxylic group to an immunogenic carrier material.

9. The antigen of claim 8 wherein said immunogenic carrier material is bovine serum albumin.

10. A method for assaying for individual norepinephrine type catecholamines selected from norepinephrine, normetanephrine, octopamine and norphenephrine in a test sample which method comprises in combination:
    (A) determining the total norepinephrine type catecholamine concentration by conducting an immunoassay on said test sample utilizing an antibody having specificity for norepinephrine type catecholamines;
    (B) treating an aliquot of said test sample with iodine at pH 7.4 so as to selectively convert any norepinephrine present in said test sample to a form which is not bound by said antibody, treating said aliquot with excess aqueous sulfite solution so as to reduce any remaining iodine, adjusting the pH of the resulting solution to that required for said immunoassay and then determining the norepinephrine type catecholamine concentration by conducting said immunoassay on said resulting solution representing the sum total of normetanephrine, octopamine and norphenephrine in said test sample;

(C) treating a second aliquot of said test sample with iodine at pH 8.6 so as to selectively convert any norepinephrine and normetanephrine present in said test sample to forms which are not bound by said antibody, treating said aliquot with excess aqueous sulfite solution, adjusting the pH to a level compatible for said immunoassay and then determining the concentration of norepinephrine type catecholamines by conducting said immunoassay on said test solution, said concentration representing the sum total of octopamine and norepinephrine present in said test sample; and (D) treating a third aliquot of said test sample with iodine at pH 9.2 so as to selectively convert any norepinephrine, normetanephrine and octopamine present in said test sample to forms which are not bound by said antibody treating said aliquot with excess aqueous sulfite solution, adjusting the pH to a level compatible for said immunoassay and then determining the concentration of norepinephrine type catecholamine by conducting said immunoassay on said test sample, said concentration representing the norepinephrine present in said test sample;

wherein the concentration of norepinephrine is determined by subtracting the concentration found in Step (B) above from that of Step (A); the concentration of normetanephrine is determined by subtracting the concentration found in Step (C) above from that of Step (B); and the concentration of octopamine is determined by subtracting the concentration found in Step (D) above from that of Step (C).

11. The method of claim 10 wherein said immunoassay utilized is radioimmunoassay, the sample is first deproteinized, the pH of the iodination treatment of Steps (B) and (C) are maintained with phosphate buffer and the pH of the iodination treatment of Step (D) is maintained with carbonate-bicarbonate buffer.

12. An antibody specific to norepinephrine type catecholamines, said antibody being elicited by an antigen comprising rac. 4-(2-amino-1-hydroxyethyl) phenoxyacetic acid convalently bonded to an immunogenic carrier material.

* * * * *